United States Patent [19]

Fenyes et al.

[11] Patent Number: 4,581,058

[45] Date of Patent: Apr. 8, 1986

[54] POLYMERIC QUATERNARY AMMONIUM COMPOUNDS AND THEIR USES

[75] Inventors: Joseph G. Fenyes, Germantown; John D. Pera, Memphis, both of Tenn.

[73] Assignee: Buckman Laboratories, Inc., Memphis, Tenn.

[21] Appl. No.: 675,841

[22] Filed: Nov. 28, 1984

Related U.S. Application Data

[63] Continuation of Ser. No. 414,108, Sep. 2, 1982, Pat. No. 4,506,081.

[51] Int. Cl.$^4$ ............................................. A01N 25/00
[52] U.S. Cl. .......................................... 71/67; 514/252; 514/255; 514/422; 514/408; 514/642; 514/643
[58] Field of Search ...................... 71/67, 85; 528/367; 544/372, 400; 546/265; 548/523; 564/59; 514/252, 255, 422, 408, 642, 643

[56] References Cited

U.S. PATENT DOCUMENTS

| | | | |
|---|---|---|---|
| 3,324,176 | 6/1967 | Kirschnek et al. | 564/59 |
| 3,864,379 | 2/1975 | Thompson | 564/59 X |
| 3,957,774 | 5/1976 | Kalopissis et al. | 564/59 X |
| 4,247,476 | 1/1981 | Haase et al. | 564/59 X |
| 4,390,689 | 6/1983 | Jacquet et al. | 528/367 X |
| 4,395,541 | 7/1983 | Jacquet et al. | 528/367 |

*Primary Examiner*—Leonard Schenkman
*Assistant Examiner*—Joseph A. Lipovsky
*Attorney, Agent, or Firm*—Finnegan, Henderson, Farabow, Garrett and Dunner

[57] ABSTRACT

Novel polyquaternary ammonium compounds prepared from N,N'-bis(dialkylaminoalkyl)ureas, hydrochloric acid, epichlorohydrin and tertiary amines are useful as microbicides, corrosion inhibitors, debonding agents, flocculants, softeners, anti-static agents, and demulsifiers.

11 Claims, No Drawings

POLYMERIC QUATERNARY AMMONIUM COMPOUNDS AND THEIR USES

This is a continuation of application Ser. No. 414,108, filed Sept. 2, 1982, now U.S. Pat. No. 4,506,081.

This invention relates to novel polyquaternary ammonium compositions including diquaternary ammonium compounds and to their uses as microbicides, corrosion inhibitors, debonding agents, flocculants, softeners, anti-static agents and demulsifiers.

The compositions have the structure

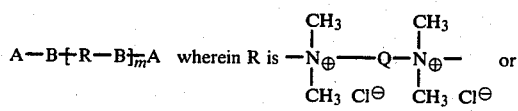

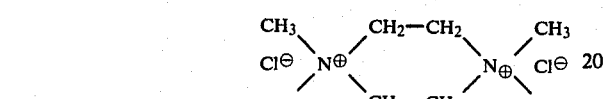

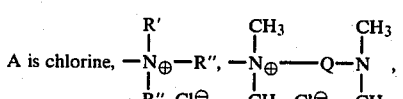

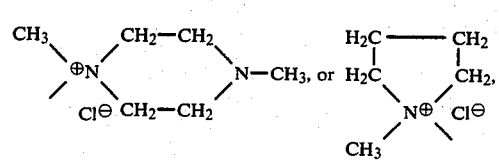

R' is methyl, ethyl, propyl, hydroxyethyl or hydroxypropyl; characterized in that R' and R" are identical when R' is an ethyl, propyl, hydroxyethyl or hydroxypropyl and when R' is methyl, R" is independently methyl or an alkyl group containing 5 to 22 carbon atoms having 0 to 2 carbon to carbon double bonds, cyclohexyl, benzyl or phenyl; further characterized in that R' and R" may form a pyridyl group; Q is $-(CH_2)_p-$, $-CH_2-CH=CH-CH_2-$, $-CH_2-CH_2-O-CH_2-CH_2-$, $-CH_2-CH(OH)-CH_2-$, or

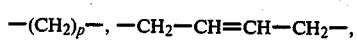

B is 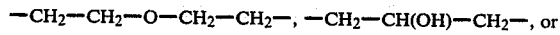

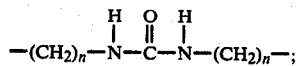

R''' is a lower alkyl group, m is 0 or a number from 1 to 100, n is 2 or 3, and p varies from 2 to 12.

All of the products of this invention are derived from N,N'-bis(dialkylaminoethyl)urea or N,N'-bis(dialkylaminopropyl)urea in which the alkyl groups are lower alkyl, such as methyl, ethyl and propyl, which hereinafter will sometimes be referred to as "urea diamine". The preparation of N,N'-bis(dimethylaminopropyl)urea from dimethylaminopropylamine and urea is described in Example 1 of U.S. Pat. No. 4,157,388.

Other diamines which can be reacted with urea include dimethylaminoethylamine, diethylaminoethylamine, diethylaminopropylamine, and other lower dialkylaminoethylamines and dialkylaminopropylamines.

A number of reaction sequences can be used, starting with the "urea diamines" to produce the novel products of this invention. These are described in the following:

1. In order to prepare the simplest di-quaternary ammonium compounds of this invention, one mole of the "urea diamine" is reacted with two moles of hydrochloric acid to make the diamine dihydrochloride which is then reacted with two moles of epichlorohydrin to produce a bis(chlorohydrin). This reaction is usually run in water or lower alkyl alcohols at a temperature varying from 50° to 110° C. When N,N'-bis(dimethylaminopropyl)urea is used in this sequence, the following compound, which we refer to as bis(chlorohydrin)A, is produced:

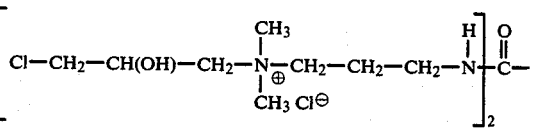

2. The bis(chlorohydrins) can be reacted in other ways to produce products of this invention. In the first type of reaction, one mole of the bis(chlorohydrin) is reacted with one or two moles of tertiary amine in such a manner as to form one or two additional quaternary ammonium groups at the extremities of the bis(chlorohydrins). The tertiary amines used for this reaction have the structure:

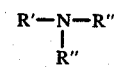

wherein R' is methyl, ethyl, propyl, hydroxyethyl or hydroxypropyl characterized in that R' and R" are identical when R' is ethyl, propyl, hydroxyethyl or hydroxypropyl. When R' is methyl, R" is independently methyl or an alkyl group containing 5 to 22 carbon atoms having 0 to 2 carbon to carbon double bonds, cyclohexyl, benzyl or phenyl. R' and R" may also form a pyridyl group. N-Methylpiperidine may also be used to cap the bis(chlorohydrins).

3. The bis(chlorohydrins exemplified by bis(chlorohydrin)A can also be reacted with equi-molar quantities of ditertiary amines to form novel polyquaternary ammonium products, known as ionene polymers. The ditertiary amines are selected from

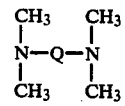

and N,N'-dimethylpiperazine, where Q is $-(CH_2)_p-$, $-CH_2-CH=CH-CH_2-$, $-CH_2CH_2-O-CH_2CH_2-$, $-CH_2CH(OH)CH_2-$ or

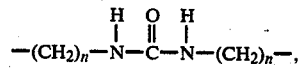

wherein p is an integer varying from 2 to 12 and n is either 2 or 3.

4. Other polymeric quaternary ammonium products of this invention are prepared by reacting X moles of the bis(chlorohydrin) at an elevated temperature in the presence of water with X-1 moles of the ditertiary amines already described in reaction type 3 above. We have found suitable reaction temperatures and times may vary from about 80° to 105° C. and from 1 to 30 hours. As used herein, X is an integer varying from 2 to 101. The molecular weight of the precursor is calculated by multiplying X times the molecular weight of the bis(chlorohydrin) used and adding X-1 times the molecular weight of the second ditertiary amine.

5. The products produced in reaction type 4 have reactive chlorine atoms at both extremities and can be reacted further with one or two moles of the monotertiary amines described hereinbefore in reaction type 2 in the presence of water or a solvent at a temperature varying from about 25° to 110° C. for a period varying from about 1 to 30 hours.

Suitable solvents in all of the reactions are water or water-soluble lower alcohols and other polar compounds.

The reactions described in reaction types 3 and 4 involve the reaction of an $\alpha,\omega$-ditertiary amine with an $\alpha,\omega$-dihalogenated alkyl compound. This reaction is known in the chemical literature as a Menschutkin Reaction and is used to prepare relatively low molecular weight polymers which are polymeric quaternary ammonium compounds known as ionene polymers. The molecular weights of these linear ionenes are generally about 50,000 or less.

The polymer chain length can be controlled by using the method of manufacture described in reaction type 4 of this invention. When two moles of the $\alpha,\omega$-dihalo compound (X moles) are reacted with one mole (X-1 mole) of the ditertiary amine, a polymer is formed. When the designation P is used for the dihalo compound and O for the ditertiary amine, the polymer could then be designated P-O-P. When 5 moles of P and 4 moles of O are reacted, the precursor then is P-O-P-O-P-O-P-O-P. The same general scheme can be used to a maximum of about 101 for P and 100 for O. Regardless of the number of moles of P and O used, there will be a halogen at either end of the precursor polymer. This precursor is then reacted with a monotertiary amine as described in reaction type 5 to "cap" the ionene with additional quaternary ammonium groups. The nature of the tertiary amine and the length of the precursor polymer chain will determine the properties of the polymers of this invention and allow for the variation of hydrophilic and hydrophobic properties.

The mono-tertiary amines which may be used to cap the bis(chlorohydrins) as described in reaction types 2 and 5 may include aliphatic, alicyclic, alkylaromatic, aromatic and heterocyclic amines. The aliphatic groups may contain one or more carbon to carbon double bonds, and may be substituted with hydroxyl groups. Examples of these amines are trimethylamine, triethylamine, N,N-dimethylstearylamine, N,N-dimethyloleylamine, N,N-dimethylcaprylamine, N,N-dimethyllaurylamine, N,N-dimethylmyristylamine, N,N-dimethylpalmitylamine, methyldistearylamine, didecylmethylamine, methyldicocoamine, methyl dihydrogenated tallow amine, 1-chloro-3-(dimethylamino)-2-propanol, N,N-dimethylaniline, pyridine, N,N-dimethylbenzylamine, triethanolamine, 2-(dimethylamino)ethanol, triisopropanolamine, N,N-bis(1-methylethyl)-2-propanamine, N,N-dimethylcyclohexylamine and N-methylpiperidine.

The ditertiary amines reacted with the bis(chlorohydrins) as described in reaction types 3 and 4 include N,N',N'-tetramethyl-$\alpha,\omega$-alkanediamines wherein the alkane group contains 2 to 12 carbon atoms exemplified by N,N,N',N'-tetramethylethylenediamine, 2,2'-oxybis(N,N-dimethylethanamine), N,N,N',N'-tetramethyl-2-butene-1,4-diamine, 1,3-bis(dimethylamino)-2-propanol, 1,4-dimethylpiperazine, N,N'-bis(dialkylaminoethyl)urea, and N,N'-bis(dialkylaminopropyl)urea wherein the alkyl groups are lower alkyl groups.

The compositions of this invention are useful in the control of slime-forming and other microorganisms, particularly in industrial processes involving water and substances that are normally susceptible to microbiological degradation or deterioration in the presence of water, in which the growth and proliferation of such microorganisms interfere in the process itself or affect the quality or character of the resulting product.

Most microbiological problems associated with industrial and commercial cooling and process water systems are caused by a mixed microflora typically composed of algae bacteria and fungi. These microorganisms can cause the formation of biological slime, plugging and fouling, deterioration of wood, and microbiologically induced corrosion.

The compounds of this invention have been found to be extremely effective in controlling microorganisms, and the concentrations which are suitable for the control of said microorganisms vary from 0.5 to 500 ppm based on the weight of the aqueous system or water being treated.

The corrosion of metals in water is an electrochemical process that occurs because of difference in electrical potential between points on the metal surface or between two metal surfaces. This difference in potential between points on the metal surface can be due to several factors such as: differences in composition, differences in crystal size, crystal orientation, discontinuous oxide film due to air or heat treatment, stress, superficial foreign matter, inclusions of dissimilar material and alloys, differences in the concentration of dissolved oxygen as compared with another, and the contact of dissimilar metals. For control of corrosion in aqueous systems concentrations of 0.5 to 500 ppm based on the weight of water treated are suitable with a preferred concentration range of 0.5 to 50 ppm. The products of this invention may be used alone or in combination with other known corrosion inhibitors.

Cellulose pulp fiber which has been formed in the conventional manner as a pulp sheet or board on a papermaking machine is normally very difficult to fiberize. However, it can be modified with debonding compositions so that the resulting sheet or board is easily fiberized by mechanical means. The compositions of this invention are used in a fiber debonding process involving the impregnation of cellulose pulp fiber to facilitate the defiberization of pulp. For this purpose, the products of this invention are used in amounts varying from 0.1 to 2.0 parts per 100 parts of cellulose pulp fiber based on the dry weight of the fiber. In addition to serving as debonding agents, the products of this invention are also used to soften paper and other cellulosic products including textiles. When softening is desired, the concentration used varies from 0.1 to 1.0 parts per 100 parts of textile fabric, paper or cellulosic pulp based on the dry weight of the material treated.

The compositions of our invention are also useful as flocculants in the clarification of incoming water supplies and industrial and municipal effluents. In particular, the new compositions may be used in recovery of the valuable materials remaining in the process waters of pulp and paper manufacture, thereby also alleviating the pollution problem of the industry. These compositions can also be used to remove any solid particulate matter remaining in the water before it is discharged, even though such matter is not of a character suitable for use but must be disposed of by microbiological decomposition or combustion or buried in a sanitary fill. They may be used in the treatment of incoming water supplies as a supplement to low-cost alum, thus achieving a reduction of process time in addition to the desired degree of completeness in the removal of finely divided solids. Similar principles apply to the removal of particulate solid matter from water discharges in industrial or municipal effluents. Useful concentrations for this purpose may vary from as low as 0.1 ppm based on the total weight of water and particulate matter to as high as 25 ppm on the same basis with a preferred range from 0.5 to 5 ppm.

The accumulation of static electricity in a wide range of modern fabrics, especially when dried in a mechanical clothes dryer, causes the material to cling and become difficult to manage. The products of this invention have been found to be effective in eliminating static electricity on fibers such as dynel, dacron, orlon, nylon, acetate, wool, and also on such plastic materials as polystyrene. For these uses, the concentrations of these products vary from 0.125% to 0.5%.

Most of the petroleum produced in the United States contains water, usually as a stable emulsion of the water in oil. Although some water-free oil may be produced in the Middle East, it is reasonable to estimate that 60 to 70% of the world production must be dehydrated before being shipped to the refineries. Emulsions of crude oil in water are generally broken by the use of chemicals known as demulsifiers. The actual separation of the oil in water takes place in special equipment which allows the water to separate from the oil by gravity assisted by heat. The products of this invention are excellent demulsifiers and can be used to break both oil-in-water or water-in-oil emulsions at concentrations of 0.5 to 500 ppm based on the weight of the emulsion.

It is, therefore, a principal object of our invention to provide novel polyquaternary ammonium compositions.

It is another object of our invention to provide methods for controlling the growth of algae, bacteria, and fungi in aqueous systems.

It is yet another object of this invention to provide methods of flocculating impurities in water and methods of improving processing of wastes.

It is yet another object of our invention to provide methods of separating crude petroleum from water.

These and other objects and advantages of the novel compositions and methods of this invention will become apparent as the description proceeds.

In order to disclose the nature of the present invention still more clearly, the following illustrative examples will be given. It is to be understood, however, that the invention is not to be limited to the specific conditions or details set forth in these examples except insofar as such limitations are specified in the appended claims.

EXAMPLE 1

Preparation of 1,3-bis(dimethylaminoethyl)urea

A two-liter, four-necked reaction flask fitted with a reflux condenser, mechanical stirrer, thermometer and a gas inlet tube was charged with 507.7 g (5.76 moles) of dimethylaminoethylamine and 172.9 g (2.88 moles) of urea. While stirring and heating, $N_2$ was bubbled through the reaction mass carrying $NH_3$ gas out and into a sulfuric acid trap. Reflux began at 110° C. Heating was continued for approximately 15 hours as the temperature rose to 214° C. Analysis showed that 5.8 moles of the sulfuric acid had been neutralized by the ammonia and the equivalent weight of the product was found to be 101.8 (Theoretical = 101.1). The product was a clear light amber color.

EXAMPLE 2

Preparation of Bis(chlorohydrin) A

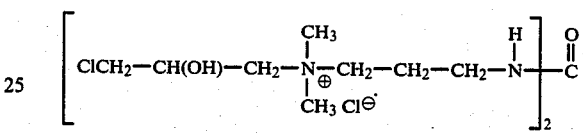

A five-liter, four-necked reaction flask fitted with a reflux condenser, mechanical stirrer, thermometer and a dropping funnel was charged with 996.6 g (4.0 moles) of 1,3-bis(dimethylaminopropyl)urea of 92.5 percent purity. This compound was prepared by the method described in U.S. Pat. No. 4,157,388. The contents of the flask were chilled by immersion into an ice-water bath, and 788.4 g (8.0 moles) of 37 percent hydrochloric acid was added at such a rate as to keep the temperature below 48° C. To the well-agitated 1,3-bis(dimethylaminopropyl)urea dihydrochloride solution so obtained, 740.0 g (8.0 moles) of epichlorohydrin was added slowly, taking care that the temperature did not exceed 48° C. After this addition was completed, the solution was kept at 45°–48° C. for one-half hour and then heated at 70° C. for another 30 minutes. A 77.3 percent equeous solution of the title compound was obtained.

EXAMPLE 3

Preparation of Bis(chlorohydrin) B

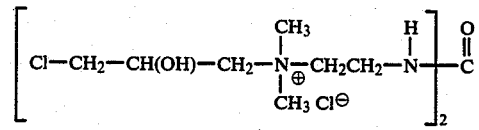

A one-liter, four-necked reaction flask fitted with a reflux condenser, mechanical stirrer, thermometer and a dropping funnel was charged with 101.1 g (0.5 mole) of 1,3-bis(2-dimethylaminoethyl)urea prepared in Example 1 and 167.7 g of water. The solution was chilled by immersion in an ice-water bath, and 98.7 g (1.0 mole) of 37 percent hydrochloric acid was added at such a rate as to keep the temperature below 48° C. To the well-agitated 1,3-bis(2-dimethylaminoethyl)urea dihydrochloride solution so obtained, 92.5 g (1.0 mole) of epichlorohydrin was added slowly, taking care that the temperature did not exceed 48° C. After this addition was completed, the solution was kept at 45°–48° C. for 30 minutes and then heated at 70° C. for another 30 minutes. A 50 percent aqueous solution of the title compound was obtained.

EXAMPLES 4 TO 9

Various quantities of the 77.3 percent aqueous solution of bis(chlorohydrin) A prepared in Example 2 were reacted at reflux temperatures in water with a number of tertiary amines at a ratio of two moles of tertiary amine to one mole of the bis(chlorohydrin) A. These reactions are included in Table 1.

TABLE 1

| Example | Tertiary Amine | Time of Reaction Hours | Solids Content Percent |
|---|---|---|---|
| 4 | N,N—dimethylcaprylamine | 6 | 50 |
| 5 | N,N—dimethylmyristylamine | 6 | 50 |
| 6 | N,N—dimethylstearylamine | 6 | 25 |
| 7 | N—methyldistearylamine | 8 | 15 |
| 8 | N—methylpiperidine | 2 | 50 |
| 9 | triethanolamine | 5 | 40 |

EXAMPLES 10 TO 14

Various quantities of the 50 percent aqueous solution of bis(chlorohydrin) B prepared in Example 3 were reacted at reflux temperatures in water with a number of tertiary amines at a ratio of two moles of tertiary amine to one mole of the bis(chlorohydrin) B. These reactions are included in Table 2.

TABLE 2

| Example | Tertiary Amine | Time of Reaction Hours | Solids Content Percent |
|---|---|---|---|
| 10 | N,N—dimethylcaprylamine | 6 | 50 |
| 11 | N,N—dimethylmyristylamine | 6 | 50 |
| 12 | N,N—dimethylstearylamine | 6 | 25 |
| 13 | N—methyldistearylamine | 8 | 15 |
| 14 | triethanolamine | 5 | 40 |

EXAMPLE 15

Reaction of bis(chlorohydrin) A with two moles of N,N,N',N'-tetramethylethylenediamine Into a one-liter, four-necked reaction flask equipped with a reflux condenser, a mechanical stirrer, thermometer, and a dropping funnel were placed 157.9 g (0.25 mole) of 77.3 percent solution of bis(chlorohydrin) A prepared in Example 2 and 99.7 g of water. This solution was heated to between 40° and 50° C. while agitating by means of the mechanical stirrer. Then 83. g (0.5 mole) of a 70 percent aqueous N,N,N',N'-tetramethylethylenediamine was slowly introduced. The resulting mixture was heated at reflux temperature for 2 hours and the product was obtained as a clear, dark amber-colored solution containing 50 percent solids.

EXAMPLE 16

Reaction of bis(chlorohydrin) A with two moles of 1,4-dimethylpiperazine

Similarly to the procedure given in Example 15, 157.9 g (0.25 mole) of a 77.3 percent aqueous solution of bis(chlorohydrin) A prepared in Example 2 in 76.1 g of water was treated with 124.4 g (0.5 mole) of a 45.9 percent aqueous solution of 1,4-dimethylpiperazine. The polyquaternary ammonium chloride product, containing tertiary amine end groups was obtained in a 50 percent concentration as a dark amber colored solution.

EXAMPLES 17 TO 22

Reactions of bis(chlorohydrin) A with ditertiary amines at 1 to 1 mole ratios

Various quantities of the 77.3 percent aqueous solution of bis(chlorohydrin) A prepared in Example 2 were reacted at reflux temperature in water with a number of ditertiary amines at a mole ratio of 1 to 1. These reactions are listed in Table 3.

TABLE 3

| Example | Ditertiaryamine | Time of Reaction Hours | Solids Content Percent |
|---|---|---|---|
| 17 | N,N,N',N'—tetramethylethylenediamine | 3 | 50 |
| 18 | 1,4-dimethylpiperazine | 8 | 50 |
| 19 | 2,2'-oxybis(N,N—dimethylethanamine) | 2 | 50 |
| 20 | N,N,N',N'—tetramethyl-2-butene-1,4-diamine | 2 | 50 |
| 21 | 1,3-bis(dimethylamino)-2-propanol | 2 | 50 |
| 22 | N,N'—bis(dimethylaminopropyl)urea | 6 | 50 |

EXAMPLES 23 AND 24

Reactions of bis(chlorohydrin) B with ditertiary amines at 1 to 1 mole ratio

The procedure used for Examples 17 to 22 was followed with bis(chlorohydrin) B and N,N,N',N'-tetramethylethylenediamine (Example 23) and N,N'-bis(dimethylaminopropyl)urea (Example 24). The reaction times were 3 and 6 hours respectively and the solids concentration of the products prepared was 50 percent.

EXAMPLES 25 TO 31

Reactions of X moles of bis(chlorohydrin) A with X-1 moles of ditertiary amines

Various quantities of the 77.4 percent aqueous solution of bis(chlorohydrin) A prepared in Example 2 and various ditertiary amines were refluxed for several hours in water while being vigorously stirred. The reaction products, polyquaternary ammonium salts, containing urea moieties, were obtained as solutions having total solids content as indicated in Table 4.

TABLE 4

| Example | Bis(chlorohydrin) A Moles | Ditertiary Amine | Amine Moles | Solids Content Percent |
|---|---|---|---|---|
| 25 | 2 | N,N,N',N'—tetramethylethylenediamine | 1 | 50 |
| 26 | 26 | N,N,N',N'—tetramethylethylenediamine | 25 | 50 |
| 27 | 101 | N,N,N',N'—tetramethylethylenediamine | 100 | 50 |
| 28 | 10 | 1,3-bis(dimethylamino)-2-propanol | 9 | 50 |
| 29 | 45 | 1,3-bis(dimethylamino)-2-propanol | 44 | 50 |
| 30 | 26 | N,N'—bis(dimethylaminopropyl) urea | 25 | 50 |
| 31 | 75 | N,N'—bis(dimethylaminopropyl) urea | 74 | 50 |

EXAMPLES 32 TO 37

Reactions of X moles of bis(chlorohydrin) B with X-1 moles of ditertiary amines

Various quantities of the 50 percent aqueous solution of bis(chlorohydrin) B prepared in Example 3 and various ditertiary amines were refluxed for several hours in water or mixtures of isopropanol and water while being vigorously stirred. The poly(quaternary ammonium)-salts obtained as solutions having total solids content as indicated in Table 5.

TABLE 5

| Example | Bis(chlorohydrin) A Moles | Ditertiary Amine | Amine Moles | Solids Content Percent |
|---|---|---|---|---|
| 32 | 2 | N,N,N',N'—tetramethyl ethylenediamine | 1 | 50 |
| 33 | 50 | N,N,N',N'—tetramethyl ethylenediamine | 49 | 50 |
| 34 | 2 | 1,3-bis(dimethylamino)-2-propanol | 1 | 50 |
| 35 | 40 | 1,3-bis(dimethylamino)-2-propanol | 39 | 50 |
| 36 | 2 | N,N'—bis(dimethylaminopropyl) urea | 1 | 50 |
| 37 | 30 | N,N'—bis(dimethylaminopropyl) urea | 29 | 50 |

EXAMPLES 38 TO 49

Reactions of bis(chlorohydrins) with tertiary amines

The new bis(chlorohydrins) prepared in Examples 25 to 30 from bis(chlorohydrin) A and ditertiary amines were capped with quaternary ammonium groups by reacting one mole of the said bis(chlorohydrin) with two moles of mono tertiary amines. These reactions were run at reflux using solvents such as water, alcohols or mixtures of water and alcohols as described in Table 6.

TABLE 6

| Example | Chlorohydrin used Example | Solvent | Time at reflux Hours | Tertiaryamine | Solids Content Percent |
|---|---|---|---|---|---|
| 38 | 25 | water | 4 | N,N—dimethyllaurylamine | 25 |
| 39 | 25 | water | 5 | N,N—dimethylmyristylamine | 25 |
| 40 | 25 | water | 5 | N,N—dimethylpalmitylamine | 25 |
| 41 | 25 | water/propylene glycol | 8 | N,N—dimethylstearylamine | 25 |
| 42 | 25 | water | 4 | triethanolamine | 50 |
| 43 | 26 | water/isopropanol | 6 | N,N—dimethyllaurylamine | 25 |
| 44 | 26 | water/isopropanol | 6 | N,N—dimethylmyristylamine | 25 |
| 45 | 26 | water/propylene glycol | 8 | N,N—dimethylpalmitylamine | 25 |
| 46 | 26 | water/propylene glycol | 12 | N,N—dimethylstearylamine | 25 |
| 47 | 26 | water | 4 | triethanolamine | 50 |
| 48 | 27 | water/isopropanol | 6 | N,N—dimethyllaurylamine | 25 |
| 49 | 27 | water | 4 | triethanolamine | 50 |

EXAMPLE 50

The effect of the novel polymeric quaternary ammonium compositions described in the preceding examples on the precentage kill of the bacterium *Enterobacter aerogenes* was determined using the method described in U.S. Pat. No. 2,881,070, with the modification described in U.S. Pat. No. 4,054,542. The results are included in Table 7.

TABLE 7

| Ionene polymer from examples | Concentration in part per million required for 80 percent kill or greater of *Enterobacter aerogenes* in a basal salt substrate after 18 hours contact | | |
|---|---|---|---|
| | pH 6.0–6.5 | pH 7.0–7.5 | pH 8.0–8.5 |
| 4 | — | — | 0.1 |
| 5 | — | — | 0.1 |
| 7 | — | — | 0.1 |
| 8 | 0.1 | 0.1 | 0.3 |
| 17 | 0.1 | 0.1 | 0.3 |
| 18 | 0.4 | 0.5 | 0.4 |
| 25 | 0.1 | 0.1 | 0.1 |

EXAMPLE 51

The effect of some of the novel polymeric quaternary ammonium compositions described in the preceding examples on the inhibition of the algae *Chlorella pyrenoidosa, Chlorococcum hypnosporum,* and *Phormidium inundatum* was determined using the procedure described in Example 2 of U.S. Pat. No. 3,771,989. The results are included in Table 8. Observations of growth were made after 28 days on the basis of the following Key:

4 = Excellent
3 = Good
2 = Poor
1 = Very poor, scant, questionable
0 = No growth

TABLE 8

| Ionene polymer from examples | Concentration in parts per million required for inhibition of growth after 28 days | | |
|---|---|---|---|
| | *Chlorella pyrenoidosa* | *Chlorococcum hypnosporum* | *Phormidium inundatum* |
| 10 | — | — | 1.0 |
| 11 | — | — | 2.0–4.0 |
| 12 | — | — | 6.0 |
| 17 | 1.0–3.0 | 2.0 | 3.0 |
| 25 | — | — | 1.0–2.0 |
| 31 | — | — | 2.0 |

EXAMPLE 52

The ionene-type polymers of this invention were used in the treatment of wet bleached pine kraft pulp in the form of an aqueous slurry with a pulp consistency of 0.5 percent. Handsheets were formed from the pulp on a laboratory handsheet machine to produce 20 cm × 20 cm pulp sheets with basis weights of 120 g/m². After the sheets were formed, pressed, and dried by the standard procedure, the bonding effect was evaluated by determining the fiber to fiber internal bonding strength of these sheets by means of a Scott Internal Bond Tester as described in TAPPI UM-403. The debonding effect was expressed as a percentage factor calculated as follows:

Internal Bond Factor =

$$\frac{\text{(Internal Bond of Treated Pulp Sheet)} \times 100}{\text{Internal Bond of Untreated Pulp Sheet}}$$

Thus, the untreated pulp would have an Internal Bond Factor of 100 and debonded pulp would have an Internal Bond Factor below 100. The higher this factor, the greater the degree of bonding achieved.

Table 9 shows the results obtained with the ionene polymers when they were evaluated by the indicated test method. Treatment rates are in weight percent based on the dry weight of pulp.

TABLE 9

| Example | Treatment Rate Percent | Internal Bond Factor |
|---------|------------------------|----------------------|
| 7       | 0.5                    | 71                   |
| 17      | 0.5                    | 115                  |
| 25      | 0.5                    | 110                  |

The invention having thus been described, what is claimed and desired to be secured by Letters Patent is:

1. A method of inhibiting the growth and proliferation of microorganisms selected from the group consisting of algae, bacteria, and fungi which comprises contacting said microorganisms with a polymeric quaternary ammonium composition having the structure

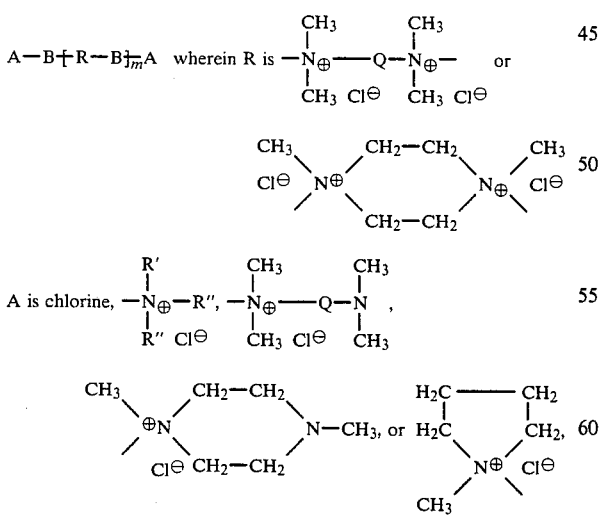

R' is methyl, ethyl, propyl, hydroxyethyl or hydroxypropyl; characterized in that R' and R" are identical when R' is an ethyl, propyl, hydroxyethyl or hydroxypropyl and when R' is methyl, R" is independently methyl or an alkyl group containing 5 to 22 carbon atoms having 0 to 2 carbon to carbon double bonds, cyclohexyl, benzyl or phenyl; further characterized in that R' and R" may form a pyridyl group; Q is

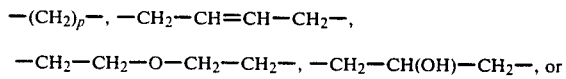

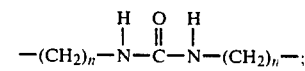

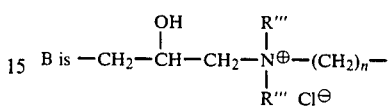

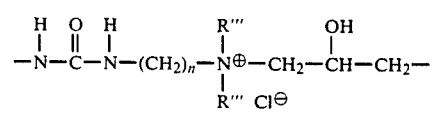

R'" is a lower alkyl group, m is 0 or a number from 1 to 200, n is 2 or 3, and p varies from 2 to 12; said polymeric quaternary ammonium composition being present in an amount sufficient to inhibit the growth and proliferation of said microorganisms.

2. The method of claim 1 wherein in said polyquaternary, B is ammonium composition A is chlorine, B is

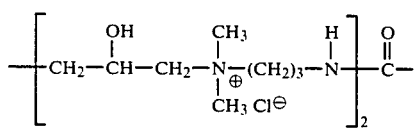

and m is 0.

3. The method of claim 1 wherein in said polyquaternary ammonium composition

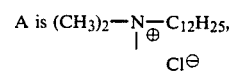

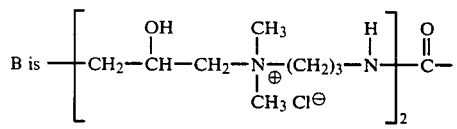

and m is 0.

4. The method of claim 1 wherein in said polyquaternary ammonium composition A is

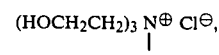

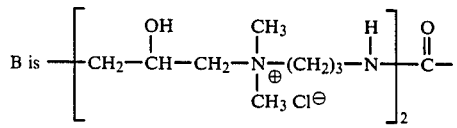

and m is 0.

5. The method of claim 1 wherein in said polyquaternary ammonium composition A is $$\begin{array}{c} H_2C\text{---}CH_2 \\ H_2C\phantom{---}CH_2 \\ N^\oplus \\ CH_3 \phantom{--} Cl^\ominus \end{array}$$

$$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

and m is 0.

6. The method of claim 1 wherein in said polyquaternary ammonium composition A is chlorine $$\text{or } \text{---}\underset{\underset{Cl^\ominus}{CH_3}}{\overset{CH_3}{N^\oplus}}\text{---}CH_2\text{---}CH_2\text{---}\underset{CH_3}{\overset{CH_3}{N}}\text{---},$$

$$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

$$R \text{ is } \text{---}\underset{\underset{Cl^\ominus}{CH_3}}{\overset{CH_3}{N^\oplus}}\text{---}CH_2\text{---}CH_2\text{---}\underset{\underset{Cl^\ominus}{CH_3}}{\overset{CH_3}{N^\oplus}}\text{---}$$

and m varies from 1 to 200.

7. The method of claim 1 wherein in said polyquaternary ammonium composition A is chlorine or $$(CH_3)_2\text{---}\underset{Cl^\ominus}{\overset{N^\oplus}{|}}\text{---}CH_2\text{---}CH(OH)\text{---}CH_2\text{---}\underset{Cl^\ominus}{\overset{N^\oplus}{|}}\text{---}(CH_3)_2$$

$$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

$$R \text{ is } (CH_3)_2\underset{Cl^\ominus}{\overset{N^\oplus}{|}}\text{---}CH_2\text{---}CH(OH)\text{---}CH_2\text{---}\underset{Cl^\ominus}{\overset{N^\oplus}{|}}(CH_3)_2$$

and m varies from 1 to 200.

8. The method of claim 1 wherein in said polyquaternary ammonium composition A is chlorine, $$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

$$R \text{ is } (CH_3)_2\text{---}\underset{Cl^\ominus}{\overset{N^\oplus}{|}}\text{---}CH_2\text{---}CH_2\text{---}\underset{Cl^\ominus}{\overset{N^\oplus}{|}}\text{---}(CH_3)_2$$

and m varies from 1 to 200.

9. The method of claim 1 wherein in said polyquaternary ammonium composition A is chlorine $$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

$$R \text{ is } (CH_3)_2\underset{Cl^\ominus}{\overset{N^\oplus}{|}}\text{---}CH_2\text{---}CH(OH)\text{---}CH_2\text{---}\underset{Cl^\ominus}{\overset{N^\oplus}{|}}(CH_3)_2$$

and m varies from 1 to 200.

10. The method of claim 1 wherein in said polyquaternary ammonium composition A is $$(CH_3)_2\text{---}\underset{Cl^\ominus}{\overset{N^\oplus}{|}}\text{---}C_{12}H_{25},$$

$$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2$$

$$R \text{ is } (CH_3)_2\text{---}\underset{Cl^\ominus}{\overset{N^\oplus}{|}}\text{---}CH_2CH_2\text{---}\underset{Cl^\ominus}{\overset{N^\oplus}{|}}(CH_3)_2$$

and m varies from 1 to 200.

11. The method of claim 1 wherein in said polyquaternary ammonium composition A is $$(CH_3)_2\text{---}\underset{Cl^\ominus}{\overset{N^\oplus}{|}}\text{---}C_{12}H_{25},$$

$$B \text{ is } \left[\text{---}CH_2\text{---}\underset{OH}{CH}\text{---}CH_2\text{---}\underset{\underset{Cl^\ominus}{CH_3}}{\overset{CH_3}{N^\oplus}}\text{---}(CH_2)_3\text{---}\underset{H}{N}\text{---}\overset{O}{\overset{\|}{C}}\text{---}\right]_2,$$

$$R \text{ is } (CH_3)_2\text{---}\underset{Cl^\ominus}{\overset{N^\oplus}{|}}\text{---}CH_2\text{---}CH(OH)\text{---}CH_2\text{---}\underset{Cl^\ominus}{\overset{N^\oplus}{|}}(CH_3)_2$$

and m varies from 1 to 200.

* * * * *

UNITED STATES PATENT AND TRADEMARK OFFICE
CERTIFICATE OF CORRECTION

PATENT NO.   :   4,581,058
DATED        :   April 8, 1986
INVENTOR(S)  :   Joseph G. FENYES and John D. PERA It is certified that error appears in the above-identified patent and that said Letters Patent is hereby corrected as shown below:

Claim 2, line 2, delete ",B is" (first occurrence).

Signed and Sealed this

Twenty-sixth Day of August 1986

[SEAL]

Attest:

Attesting Officer

DONALD J. QUIGG

Commissioner of Patents and Trademarks